United States Patent
Reimer et al.

(10) Patent No.: US 12,329,880 B2
(45) Date of Patent: Jun. 17, 2025

(54) HEAT TREATING TO IMPROVE SYNTHETIC LEAFLET MOTION AND COAPTATION

(71) Applicant: St. Jude Medical, Cardiology Division, Inc., St. Paul, MN (US)

(72) Inventors: Jay Reimer, Saint Paul, MN (US); Yousef F. Alkhatib, Edina, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 190 days.

(21) Appl. No.: 17/495,955

(22) Filed: Oct. 7, 2021

(65) Prior Publication Data
US 2022/0105238 A1     Apr. 7, 2022

Related U.S. Application Data

(60) Provisional application No. 63/088,617, filed on Oct. 7, 2020.

(51) Int. Cl.
*A61L 27/50*        (2006.01)

(52) U.S. Cl.
CPC ....... *A61L 27/50* (2013.01); *A61F 2250/0082* (2013.01); *A61L 2430/20* (2013.01)

(58) Field of Classification Search
CPC .... A61F 2/2412; A61F 2/2475; A61F 2/2415; B29K 2023/0683; A61L 31/02
See application file for complete search history.

(56) References Cited

U.S. PATENT DOCUMENTS

| | | | | |
|---|---|---|---|---|
| 4,364,127 A | * | 12/1982 | Pierce | A61F 2/2409 137/849 |
| 6,936,067 B2 | | 8/2005 | Buchanan | |
| 2006/0111773 A1 | * | 5/2006 | Rittgers | A61F 2/2475 623/2.18 |
| 2007/0118210 A1 | * | 5/2007 | Pinchuk | A61L 27/34 623/1.26 |

(Continued)

FOREIGN PATENT DOCUMENTS

| | | |
|---|---|---|
| CN | 211610219 U * | 10/2020 |
| EP | 3298988 A1 | 3/2018 |
| WO | 2021206920 A1 | 10/2021 |

OTHER PUBLICATIONS

Dielectric Manufacturing, UHMW (Ultra-High-Molecular-Weight Polyethylene), Feb. 27, 2019 (Year: 2019).*

(Continued)

*Primary Examiner* — Christie Bahena
(74) *Attorney, Agent, or Firm* — SLEMAN & LUND LLP

(57) ABSTRACT

A prosthetic heart valve includes a support structure and a valve assembly. The valve assembly includes a cuff and a plurality of leaflets, each of the prosthetic leaflets being composed of a synthetic material. The prosthetic leaflets have a closed condition in which the prosthetic leaflets coapt to restrict blood from flowing in a retrograde direction through the support structure and an open condition in which the prosthetic leaflets allow blood to flow in an antegrade direction through the structure. The synthetic material may be heat set to bias the leaflets to the open or closed condition, or to bias one portion of the leaflet to the open condition and another portion of the leaflet to the closed condition.

19 Claims, 10 Drawing Sheets

(56) References Cited

U.S. PATENT DOCUMENTS

| | | | | |
|---|---|---|---|---|
| 2011/0160836 | A1* | 6/2011 | Behan | A61F 2/06 |
| | | | | 623/1.11 |
| 2012/0172981 | A1* | 7/2012 | DuMontelle | A61F 2/2412 |
| | | | | 623/2.17 |
| 2012/0253453 | A1* | 10/2012 | Bruchman | A61F 2/2418 |
| | | | | 623/1.24 |
| 2016/0045165 | A1* | 2/2016 | Braido | A61B 5/6847 |
| | | | | 623/2.1 |
| 2017/0209262 | A1* | 7/2017 | McKinley | A61F 2/2415 |
| 2019/0374339 | A1* | 12/2019 | Bennett | A61F 2/2415 |
| 2020/0188098 | A1 | 6/2020 | Alkhatib et al. | |
| 2020/0323630 | A1* | 10/2020 | Alkhatib | A61F 2/2409 |

OTHER PUBLICATIONS

Dal-Bianco JP, Levine RA. Anatomy of the mitral valve apparatus: role of 2D and 3D echocardiography. Cardiol Clin. May 2013;31(2):151-64. doi: 10.1016/j.ccl.2013.03.001. Epub Apr. 15, 2013. PMID: 23743068; PMCID: PMC3856635. (Year: 2013).*

International Search Report issued in Appln. No. PCT/US2021/053884 dated Jan. 26, 2022 (3 pages).

* cited by examiner

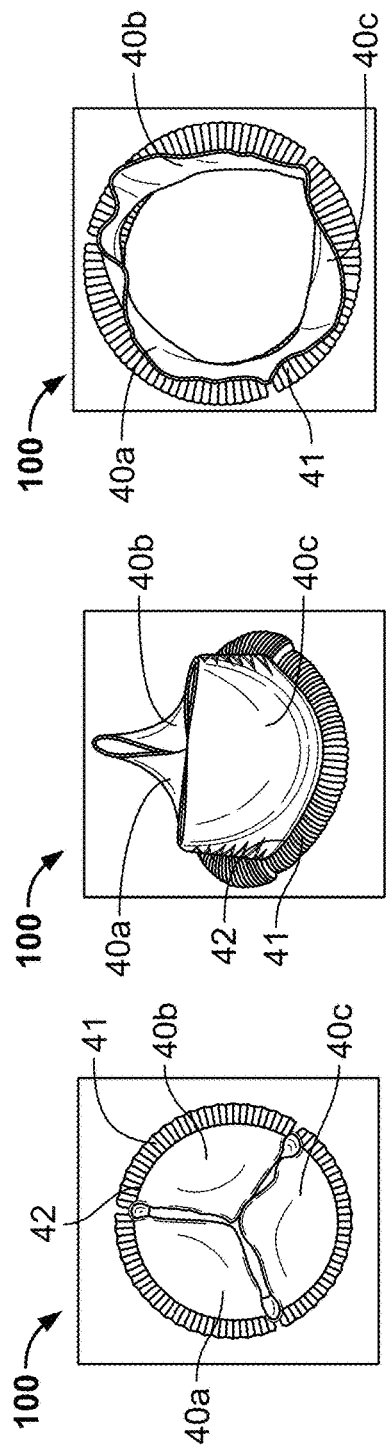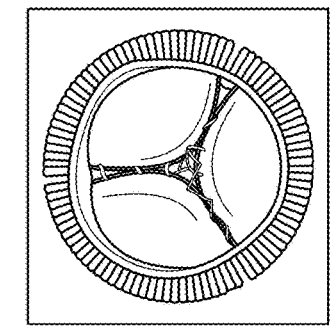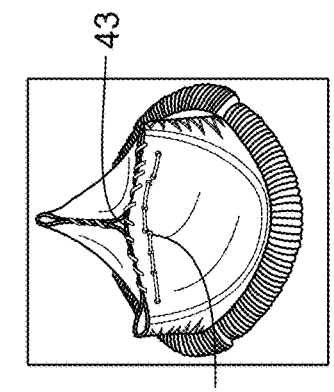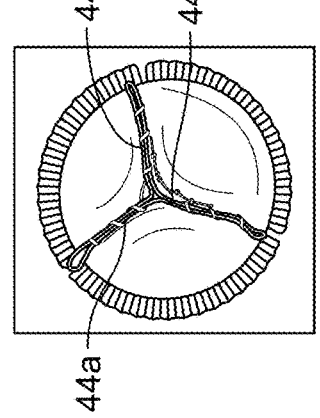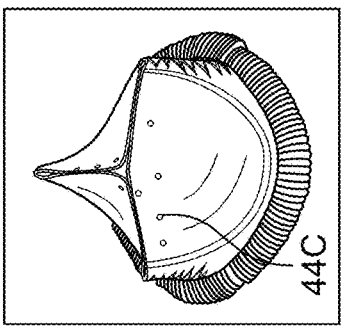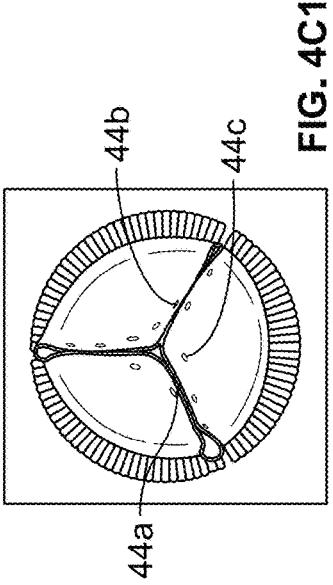

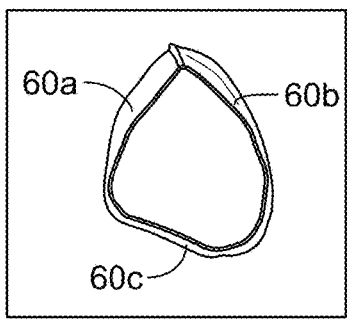
FIG. 6A1
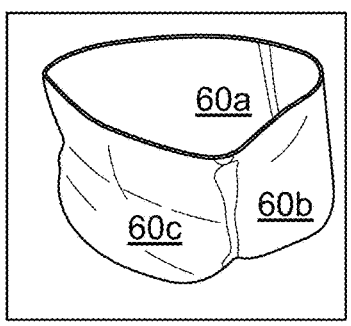
FIG. 6A2
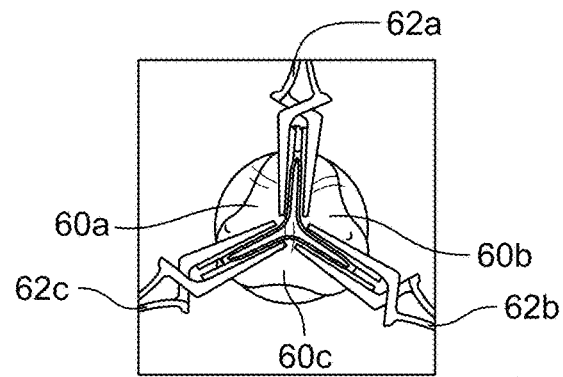
FIG. 6B1
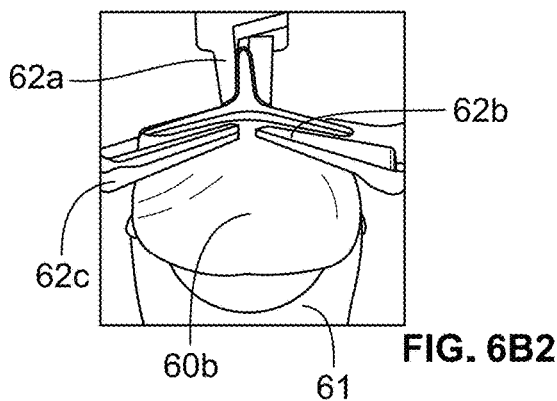
FIG. 6B2
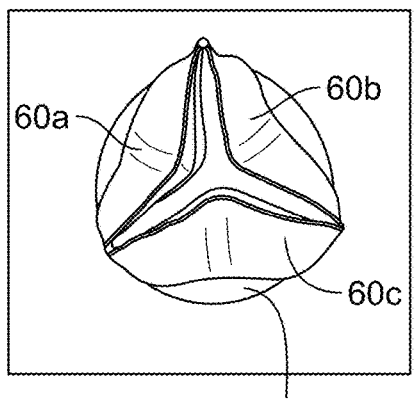
FIG. 6C1
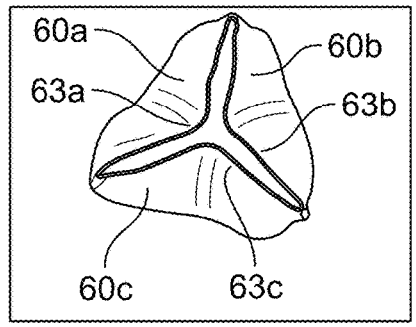
FIG. 6D1
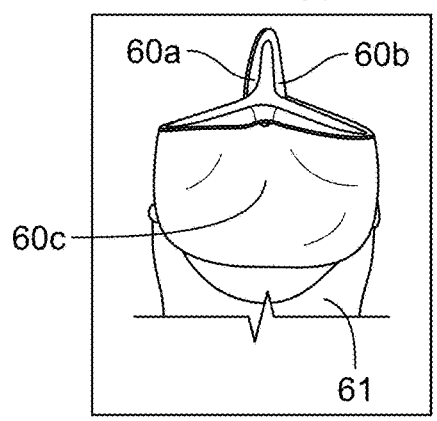
FIG. 6C2
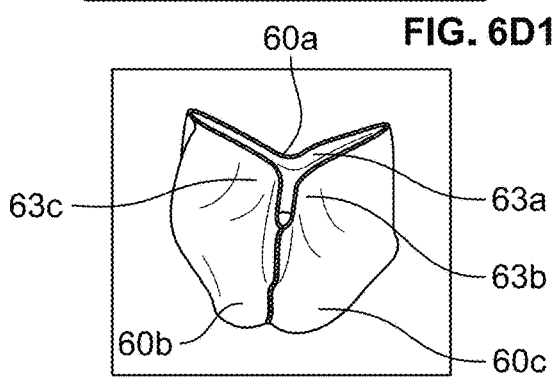
FIG. 6D2

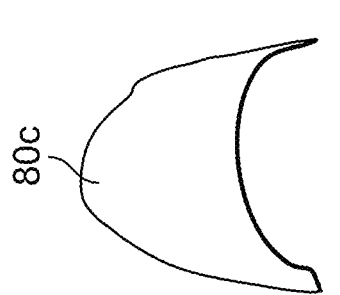
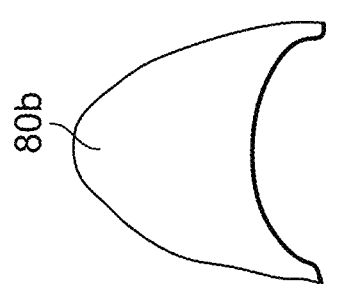
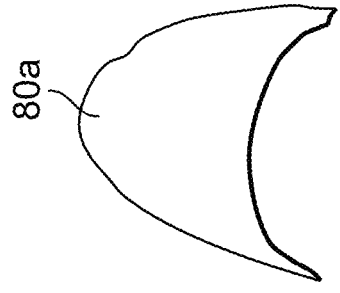
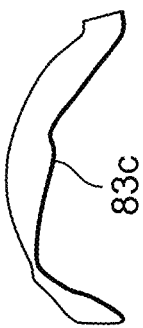
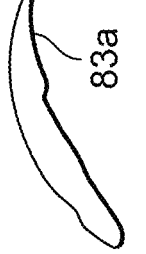
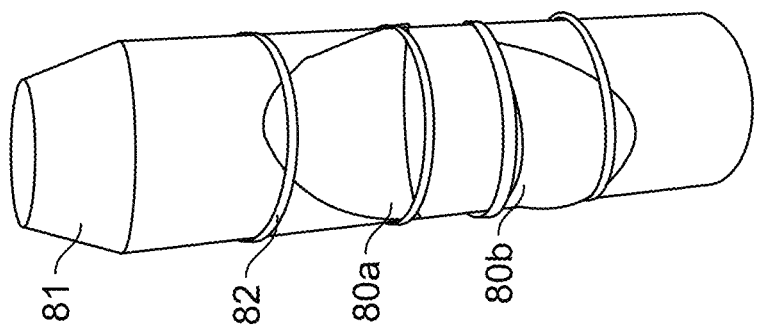

FIG. 11A
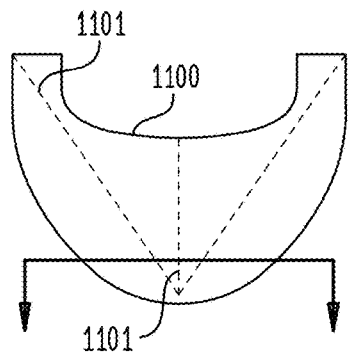
FIG. 11B
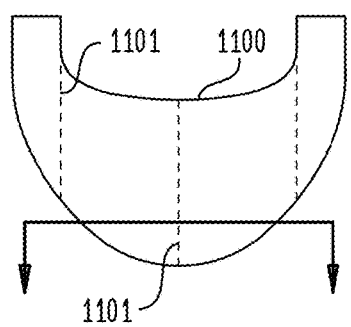
FIG. 11C
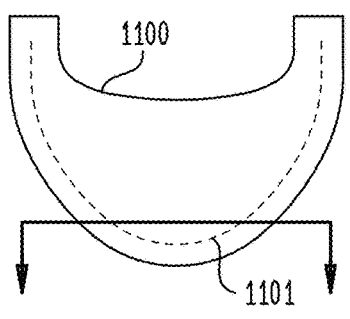
FIG. 11D
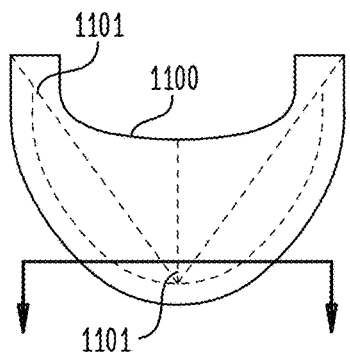
FIG. 11E
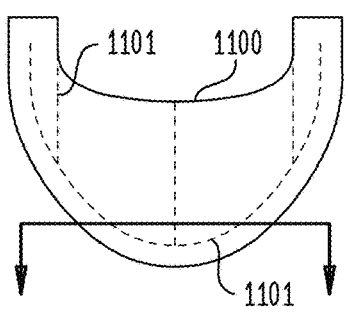
FIG. 12A1 
FIG. 12A2 
FIG. 12B1 
FIG. 12B2 

HEAT TREATING TO IMPROVE SYNTHETIC LEAFLET MOTION AND COAPTATION

CROSS-REFERENCE TO RELATED APPLICATIONS

This application claims the benefit of the filing date of U.S. Provisional Patent Application No. 63/088,617 filed Oct. 7, 2020, the disclosure of which is hereby incorporated herein by reference.

BACKGROUND OF THE DISCLOSURE

The present disclosure relates to prosthetic heart valves, and more particularly to alternative material for leaflets for use in such valves and heat treating such leaflets.

Leaflets for prosthetic heart valves may be derived from various natural tissues. Commercial natural tissues that have been chemically treated or "fixed" are often used. For example, leaflets could be made of bovine pericardium, porcine pericardium or any suitable natural animal tissue. There is increasing interest in using a synthetic material as an alternative to traditional glutaraldehyde-fixed tissue leaflets because traditional tissue leaflets tend to have shortcomings such as calcification, stenosis, and sourcing and uniformity issues. By using synthetic materials, some of these shortcomings may be addressed, but other shortcomings may arise because each alternative synthetic material exhibits different material properties that can affect valve function, such as valve durability, valve aging, and leaflet function, motion and coaptation. Alternative materials that may be used for prosthetic leaflets include various synthetic polymers including, without limitation, polytetrafluoroethylene (PTFE) or polyester, and elastic materials including silicone rubber and polyurethanes.

To improve leaflet motion in traditional leaflets, various design approaches are used, including attachment methods, leaflet size, leaflet geometry, material selection and/or the processing of the material. Despite these various approaches, additional and/or alternative measures may be useful when using a synthetic material instead of tissue in a leaflet. Therefore, there exists a need for further improvements in the design process in the production of the leaflet.

BRIEF SUMMARY OF THE DISCLOSURE

According to a first embodiment of the disclosure, a prosthetic heart valve includes a support structure, and a valve assembly attached to the support structure. The valve assembly includes a cuff and a plurality of prosthetic leaflets, each of the prosthetic leaflets being composed of a synthetic material. The prosthetic leaflets have a closed condition in which the prosthetic leaflets coapt to restrict blood from flowing in a retrograde direction (opposite the natural blood flow direction) through the support structure, and an open condition in which the prosthetic leaflets allow blood to flow in an antegrade direction (the natural blood flow direction) through the support structure. The synthetic material of at least one of the prosthetic leaflets biases the prosthetic leaflet toward either the closed condition or the open condition. In an alternative arrangement, the synthetic material may bias a portion of the leaflet to the closed condition and another portion of the leaflet to the open condition. The synthetic material may be ultra-high molecular weight polyethylene.

According to another embodiment of the disclosure, a prosthetic heart valve includes a support structure, and a valve assembly attached to the support structure. The valve assembly includes a cuff (which can be a cuff on the inside of the support structure, a cuff on the outside of the support structure, or cuffs on both the inside and the outside of the support structure) and a plurality of prosthetic leaflets, each of the prosthetic leaflets being composed of a synthetic material and having an attachment edge attached to the support structure and a free edge. The prosthetic leaflets have a closed condition in which the prosthetic leaflets coapt to restrict blood from flowing in a retrograde direction through the support structure, and an open condition in which the prosthetic leaflets allow blood to flow in an antegrade direction through the support structure. The synthetic material of one of the prosthetic leaflets may include a fold or crease formed between the attachment edge and the free edge to assist the prosthetic leaflet in transitioning between the closed condition and the open condition in a particular and repeatable desired movement. The synthetic material of the one prosthetic leaflet may include a first fold or crease extending from an apex of the attachment edge of the leaflet to a trough of the free edge of the leaflet in a direction substantially parallel the antegrade direction of blood flow through the support structure. The synthetic material of the one prosthetic leaflet may include a second fold or crease and a third fold or crease each extending from the attachment edge of the leaflet to the free edge of the leaflet. The second fold or crease and the third fold or crease may each be substantially parallel to the first fold or crease, and the first fold or crease may be positioned between the second fold or crease and the third fold or crease. The second fold or crease and the third fold or crease may each extend in substantially opposite diagonal directions from the attachment edge of the leaflet to the free edge of the leaflet, and the first fold or crease may be positioned between the second fold or crease and the third fold or crease. The synthetic material of the one prosthetic leaflet may include a first fold or crease extending in an arcuate direction substantially matching a curvature of the attachment edge of the leaflet.

According to another embodiment of the present disclosure, a method of manufacturing a prosthetic heart valve includes preparing a synthetic material; forming a bias in the synthetic material by heat setting the synthetic material at a temperature of between about 90° C. and about 170° C. for between about 20 seconds and about 30 minutes; coupling the synthetic material to a support structure to form one or more leaflets so that the leaflets may be (i) biased toward a closed condition in which the leaflets coapt to restrict blood from flowing in a retrograde direction through the support structure, or (ii) biased toward an open condition in which the leaflets allow blood to flow in an antegrade direction through the support structure. In an alternative, a portion of at least one leaflet may be biased toward the closed condition and another portion of the at least one leaflet may be biased toward the open condition. The method may further include disposing the synthetic material on a mandrel before heat setting the synthetic material. The mandrel may have a cylindrical shape with a diameter that is substantially equal to a diameter of the support structure when the support structure is in an operative condition. Disposing the synthetic material on the mandrel may include shaping the synthetic material into a shape that corresponds to the closed condition or shaping the synthetic material into a shape that corresponds to the open condition. The synthetic material may be a single strip of synthetic material during the heat setting of the synthetic material, and the single strip of synthetic material may form a plurality of the leaflets after being coupled to the support structure. The synthetic material may be formed as a single leaflet during the heat setting of the synthetic material, and, after coupling the synthetic material to the support structure, the single leaflet may be one leaflet of a plurality of leaflets coupled to the support structure. The method may also include securing the synthetic material to the mandrel at a number of locations spaced around a circumference of the mandrel prior to heat setting the synthetic material, wherein the number of locations correspond to a number of leaflets formed by the single strip of synthetic material. The synthetic material may be coupled to the support structure prior to heat setting the synthetic material. Heat setting the synthetic material may include pressing the synthetic material into a base of a mold using an insert and applying heat while the insert presses the synthetic material into the base of the mold.

BRIEF DESCRIPTION OF THE DRAWINGS

Various embodiments of the present disclosure will now be described with reference to the appended drawings. It is to be appreciated that these drawings depict only some embodiments of the invention and are therefore not to be considered limiting of its scope.

FIGS. 4A1-4A2 are top and perspective views, respectively, of a prosthetic heart valve with the leaflets in the closed position before heat setting the leaflets, according to one embodiment of the present disclosure;

FIG. 4A3 is a top view of the prosthetic heart valve of FIGS. 4A1-4A2 with the leaflets in the open position before heat setting the leaflets;

FIGS. 4B1-4B3 are top, perspective, and bottom views, respectively, of the prosthetic heart valve of FIGS. 4A1-4A2 with the leaflets sutured in the closed position;

FIGS. 4C1-4C2 are top and perspective views, respectively, of the prosthetic heart valve of FIGS. 4B1-4B3 with the leaflets in the closed position after heat setting has been performed and the temporary sutures have been removed;

FIGS. 6A1-6A2 are top and perspective views, respectively, of a leaflet strip for use in a prosthetic heart valve before heat setting;

FIGS. 6B1-6B2 are top and perspective views, respectively, of the leaflet strip of FIGS. 6A1-6A2 illustrating contouring of the leaflet strip on a mandrel before heat setting;

FIGS. 6C1-6C2 are top and perspective views, respectively, of a contoured leaflet strip after heat setting while the leaflet strip remains on a mandrel;

FIGS. 6D1-6D2 are top and perspective views, respectively, of the contoured leaflet strip of FIGS. 6C1-6C2 removed from the mandrel after heat setting;

FIG. 8A is a perspective view of individual leaflets attached to a mandrel in the open position before heat setting according to another embodiment of the present disclosure;

FIGS. 8B1-8B2 are top and side views, respectively, of the leaflets of FIG. 8A after heat setting and removal from the mandrel;

FIG. 11A is a schematic drawing of a leaflet showing folds that have been created in the leaflet according to an embodiment of the present disclosure;

FIG. 11B is a schematic drawing of a leaflet showing folds that have been created in the leaflet according to another embodiment of the present disclosure;

FIG. 11C is a schematic drawing of a leaflet showing folds that have been created in the leaflet according to another embodiment of the present disclosure;

FIG. 11D is a schematic drawing of a leaflet showing folds that have been created in the leaflet according to another embodiment of the present disclosure;

FIG. 11E is a schematic drawing of a leaflet showing folds that have been created in the leaflet according to another embodiment of the present disclosure;

FIGS. 12A1 and 12A2 show two versions of a cross-section of the leaflet taken along line A-A of FIG. 11A;

FIGS. 12B1 and 12 B2 show two versions of a cross-section of the leaflet taken along line A-A of FIG. 11B.

DETAILED DESCRIPTION

Figure 1:
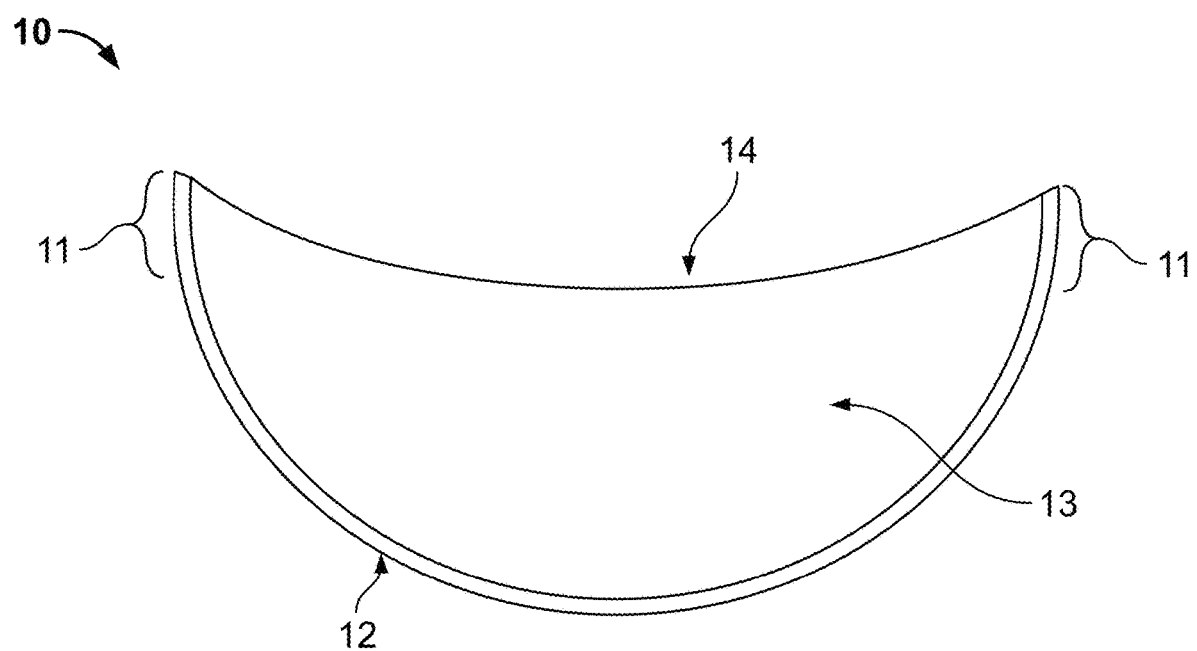
FIG. 1 is a highly schematic drawing of a leaflet identifying the pertinent regions of the leaflet.

As used herein in connection with a prosthetic heart valve, the term "inflow end" refers to the end of the heart valve through which blood enters when the valve is functioning as intended, and the "outflow end" refers to the end of the heart valve through which blood exits when the valve is functioning as intended. As used herein, the terms "proximal" and "upstream" refer to the inflow end of a prosthetic heart valve and these terms may be used interchangeably. The terms "distal" and "downstream" refer to the outflow end of a prosthetic heart valve and also may be used interchangeably. As used herein, the terms "generally," "substantially," "approximately," and "about" are intended to mean that slight deviations from absolute are included within the scope of the term so modified. Like numbers refer to similar or identical elements throughout.

The present disclosure presents a heat treatment for treating synthetic material used in the prosthetic leaflets of a prosthetic heart valve. The synthetic material may include, for example, polyolefins such as polytetrafluoroethylene (PTFE) (including expanded, stretched, low molecular weight, medium molecular weight, high molecular weight and ultra-high molecular weight (UHMW)), polyethylenes (including low, medium, high and ultra-high molecular weight polyethylene (UHMWPE—e.g., having an average molecular weight of between about 2 and about 7.5 million atomic mass units)), and polypropylene (including low, medium, high and ultra-high molecular weight polypropylene (UHMWPP)), as well as polyurethane, polyether ether ketone (PEEK), polyvinyl alcohol, silicone, rayon, polyesters, aramid, spandex, or combinations thereof. The synthetic material also may include, and is not limited to, Preclude® (ePTFE) available from W. L. Gore & Associates, Inc., and Xience-drug coated UHMWPE available from Abbott Cardiovascular Systems Inc.

The heat treatment for the synthetic material may be used to improve leaflet functionality including leaflet motion, coaptation, durability and other performance characteristics for prosthetic valves that have leaflets fabricated with a synthetic material. The heat treatment for the synthetic material includes heat setting a leaflet using heat, pressure or a combination thereof. Heat setting according to the present disclosure may be used to treat the synthetic material in a variety of ways. In one embodiment, the synthetic material may be used to shape a leaflet which is attached to a prosthetic heart valve. The assembled prosthetic heart valve including synthetic leaflets may undergo heat setting by applying heat, pressure or a combination thereof to confer the desired shape to the leaflet. When the prosthetic leaflet components are heat set after being attached in the valve, the heat and/or pressure may be applied to the leaflets while the leaflets are in the open, partially open, closed and/or partially closed configuration. Different portions of the leaflets may also be heat set in different configurations. In one embodiment, the commissure regions of the leaflet may be heat set to a closed configuration, while the middle of the leaflet may be heat set to an open configuration. In another arrangement, the free edge of the leaflet may be heat set to the closed configuration, while the belly of the leaflet is heat set to the open configuration. When heat setting is performed in different configurations, the leaflets may be heat set in the different configurations simultaneously, or in sequential treatments. When the leaflets (e.g., the valve assembly formed by the plurality of leaflets) are in the open position, the individual leaflets extend generally downstream to accommodate blood flow from the inflow end of the stent to the outflow end. When the leaflets are in the closed position, the leaflets coapt with one another other and free edge portions of the leaflets generally extend radially inwardly toward a central longitudinal axis of the stent. In other embodiments, the leaflet(s) may be heat set before the leaflet is attached to the stent or to a prosthetic heart valve. The synthetic leaflet may undergo heat setting by applying heat, pressure or a combination thereof to confer the desired shape to the leaflet before being attached to a prosthetic heart valve.

In an embodiment of the present disclosure, heat setting a leaflet made from UHMWPE may improve leaflet coaptation and may achieve more uniform opening. The heat setting process may provide a three-dimensional geometry of the leaflet(s) that is more amenable to leaflet motion and coaptation. Further, this three-dimensional geometry may be manipulated and controlled by using fixtures and/or suture patterns, as described in greater detail below.

The present disclosure will now be described with reference to the drawings, focusing primarily on the use of ultra-high molecular weight polyethylene (UHMWPE) as the synthetic material used in fabricating the leaflet. The disclosure will also be described focusing primarily on a prosthetic heart valve having three leaflets that coapt in a central area of the prosthetic heart valve. However, it should be understood that materials other than UHWMPE that have generally similar characteristics may also be used to form the prosthetic leaflets subject to heat treatment, although the heat treatment parameters may be somewhat different. Further, while the following describes a prosthetic heart valve having three leaflets, it should be understood that any number of leaflets can be used as needed in the prosthetic heart valve, including for example two leaflets or four leaflets. And it should be clear that this disclosure applies to both surgical prosthetic heart valves (e.g., those that are implanted via an open heart, open chest procedure and which are sutured into the heart) as well as collapsible and expandable heart valves (e.g., transcatheter valves that are delivered via the patient's vasculature in a collapsed condition, and which are expanded into the native valve annulus without being sutured into the heart). Finally, although the present disclosure may refer to the attachment of leaflets to a stent, such as a collapsible and expandable stent, it is contemplated that the leaflets may be attached to any support structure, including those having a generally fixed size.

FIG. 1 is a highly schematic drawing of a prosthetic leaflet 10 and pertinent regions of the leaflet 10 as known in the art. The leaflet 10 includes regions 11 that form commissures with adjacent leaflets, an attachment edge or sewing region 12, a belly 13 and a free coaptation edge 14. The commissure regions 11 represent high stress regions of the leaflet at which the leaflet may be mounted to the support structure of the prosthetic heart valve. The leaflet 10 may also attach to the support structure along the sewing region 12 which extends between the commissure regions 11. In some embodiments, the commissure regions 11 may include tabs or other additional structures to assist in coupling commissure regions of adjacent leaflets to each other and/or to a commissure attachment feature of a support structure, such as a stent. When the sewing regions 12 and commissure regions 11 of leaflets 10 are attached to the stent, the bellies 13 and free edges 14 of the leaflets are capable of moving toward each another to coapt to prevent retrograde blood flow back through the valve assembly, and away from each other toward the stent to allow antegrade blood flow through the valve assembly.

Various methods of forming the leaflets, may be used. These include mechanical methods, for example cutting the leaflet from a sheet of material with scissors or a blade. Other techniques of creating the leaflets and/or forming the leaflet assembly include, for example, forming the leaflets using cautery; stamping the leaflets from sheets of material; laser cutting the leaflets from larger pieces of material; water jet cutting the leaflets from larger pieces of material; using bio-glue to couple the leaflets to each other and/or to a support structure; and folding or laminating material to create the leaflets.

In some embodiments, leaflets formed of UHMWPE may have one or more of: a thickness of about 250 µm or less, a tensile strength of at least about 75 N and preferably at least about 90 N; a stiffness/flexural rigidity of about 3.0+/−1.75 cm; a permeability of about 850-950 mL/cm2/min; a suture retention meeting ISO7198; a stretch/strain of about 20-25%; and a tear strength meeting or exceeding ASTM D2261-13. For a leaflet formed of an expanded or stretched PTFE, the overall properties can be similar. It should be noted that the "permeability" characteristic described above may apply particularly to fabrics that are coated with another material, or uncoated fabrics that have had exposure to blood for a length of time in which the interaction of blood with the fabric reduces the permeability of the uncoated fabric.

Figure 2A:
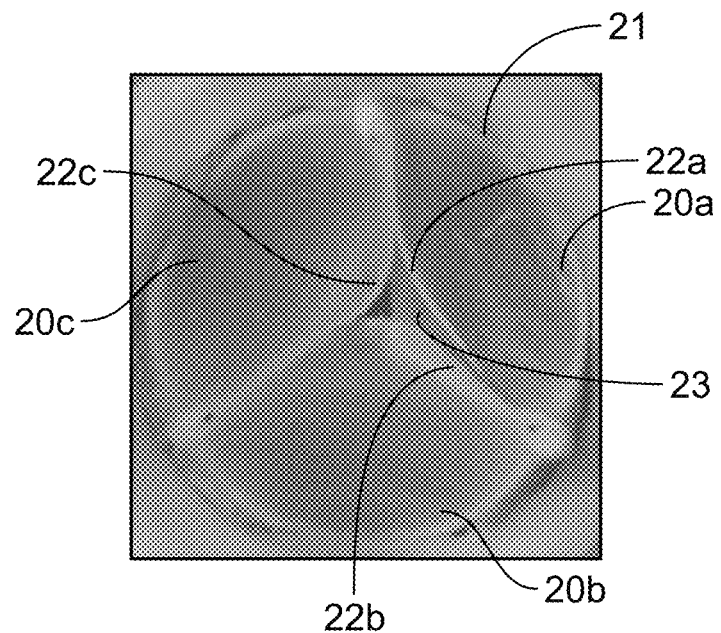
FIG. 2A is top view of leaflets in the closed position of a prosthetic heart valve before heat setting the leaflets.
Figure 2B:
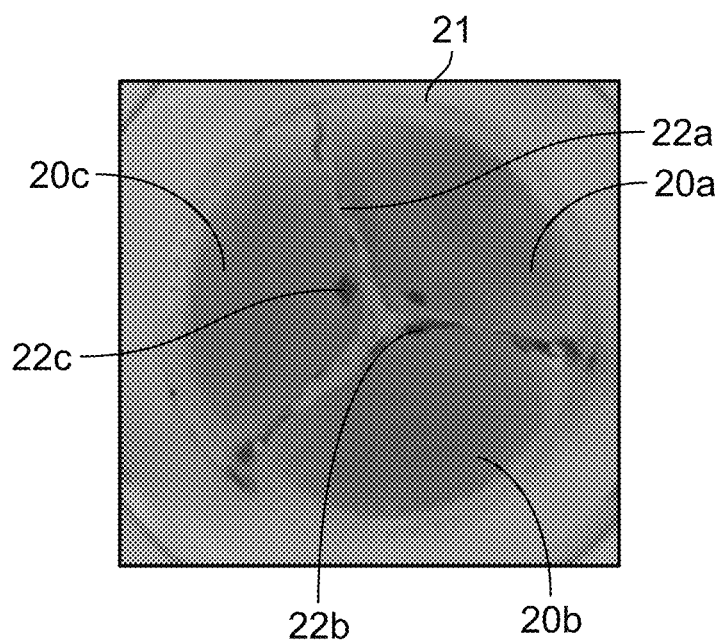
FIG. 2B is a top view of leaflets in the closed position of a prosthetic heart valve after heat setting the leaflets.

FIG. 2A is top view of leaflets 20a, 20b, 20c fabricated from UHMWPE in a closed position before heat setting. The leaflets 20a, 20b, 20c are attached to a support 21 (such as a collapsible or non-collapsible stent) as understood by one of skill in the art to form a prosthetic heart valve. In FIG. 2A, the leaflets 20a, 20b, 20c are in the maximum closure position (e.g., coapted with each other to prevent retrograde blood flow). Without heat setting the leaflets 20a, 20b, 20c, the free edges 22a, 22b, 22c of the leaflets 20a, 20b, 20c may not fully coapt in the center, leaving a gap 23. Such a gap 23 may lead to regurgitation through the valve, resulting in inefficient blood flow through the valve. One potential reason for this gap 23 is that one of the leaflets 20a, 20b, 20c may prolapse. FIG. 2B is a top view of leaflets 20a, 20b, 20c in a closed position of the prosthetic heart valve after heat setting the leaflets 20a, 20b, 20c while the leaflets are in a closed position. FIG. 2B also shows that the leaflets 20a, 20b, 20c may be heat set while in the maximum closure position. In FIG. 2B, the leaflets 20a, 20b, 20c of FIG. 2A are heat set to allow for improved coaptation, in which the free edges 22a, 22b, 22c can fully coapt in the center. As can be seen comparing FIGS. 2A and 2B, prior to heat setting, the leaflets 20a, 20b, 20c fail to completely coapt and create a gap 23, whereas after heat setting, the leaflets 20a, 20b, 20c fully coapt and eliminate (or otherwise substantially reduce the size of) any gap 23. To heat set the leaflets, heat, pressure or a combination of both are applied to the valve. It should be understood that, even if the gap 23 shown in FIG. 2A exists in the absence of applied forces, the gap may partially or completely close under back pressure from blood. Even so, it may still be beneficial to heat set the leaflets to close the gap, as shown in FIG. 2B. One benefit of heat setting in this scenario is to give the leaflet(s) a type of pre-shaped memory to help prescribe the general shape and motion of the leaflet following heat setting.

In one embodiment, the heat setting process may be performed for between about 20 seconds and about 30 minutes. In additional embodiments, the heat setting process may be performed for between about 2 minutes and about 20 minutes, or between about 5 minutes and about 10 minutes, but is not limited to these times. In one embodiment, the heat setting process may also be performed at a temperature between about 90° C. and about 170° C. In additional embodiments, the heat setting process may be performed at a temperature between about 110° C. and about 150° C., or between about 120° C. and about 135° C.

Figure 3A:
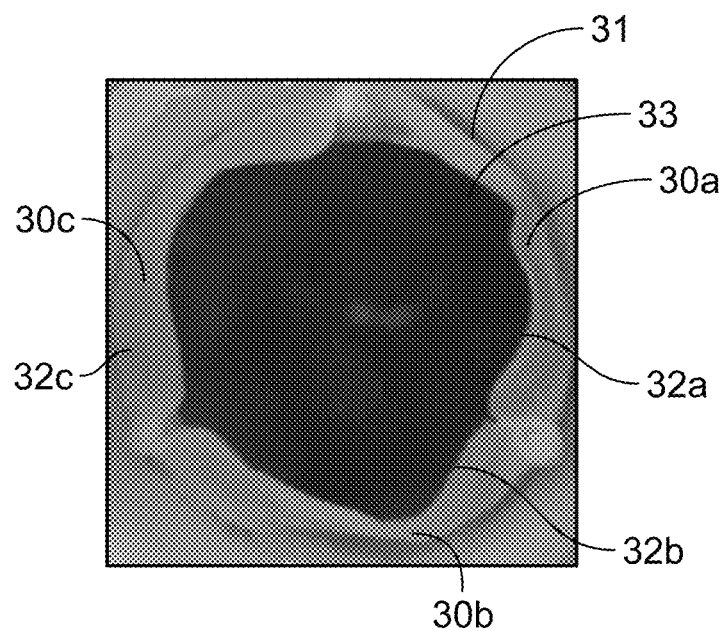
FIG. 3A is a top view of leaflets in an open position of a prosthetic heart valve before heat setting the leaflets.
Figure 3B:
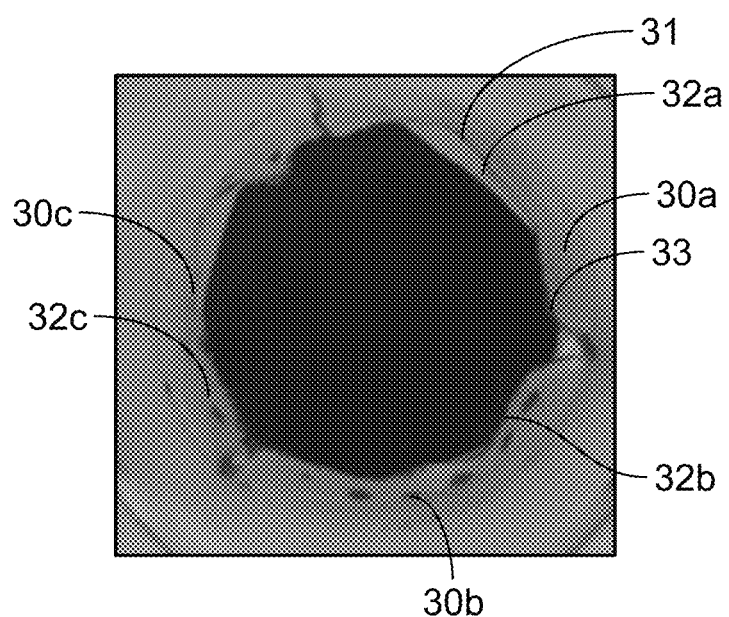
FIG. 3B is a top view of leaflets in an open position of a prosthetic heart valve after heat setting the leaflets.
Figure 5:
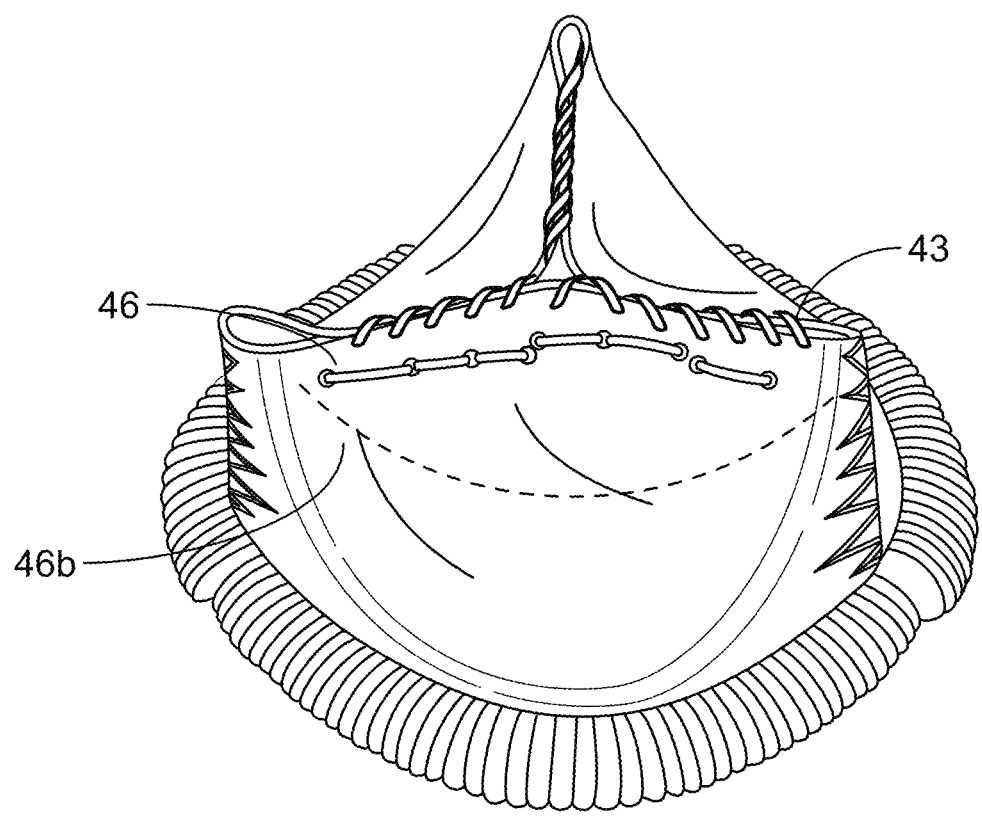
FIG. 5 is a schematic drawing of a prosthetic heart valve with leaflets in the closed position before heat setting, showing an additional embodiment of the present disclosure with an alternate temporary suture compared to the embodiment shown in FIGS. 4B1-4B3.

FIG. 3A is a top view of leaflets 30a, 30b, 30c fabricated from UHMWPE in an open position. The leaflets 30a, 30b, 30c may be attached to a support 31 (such as stent) to form a prosthetic heart valve. The leaflets 30a, 30b, 30c are illustrated in FIG. 3A before heat setting. The leaflets 30a, 30b, 30c are in a maximum opening position in FIG. 3A. When in the maximum opening position, the leaflets 30a, 30b, 30c are not uniformly open because the free edges 32a, 32b, 32c extend into the valve opening area 33. Thus, when the leaflets 30a, 30b, 30c are in the fully open condition, a smaller amount of blood is able to flow through the prosthetic heart valve compared to having the leaflets 30a, 30b, 30c not extend into the valve opening area 33. In other words, the leaflets 30a, 30b, 30c in FIG. 3A may be less likely to open to their maximum possible extent, resulting in a relatively smaller volume of blood flowing through the leaflets than if they were opened to a larger extent. In contrast, after the leaflets 30a, 30b, 30c are heat set while in an open position, the leaflets 30a, 30b, 30c may open to the maximum opening position in which the free edges 32a, 32b, 32c do not extend into the valve opening area 33 but are uniformly open as illustrated in FIG. 3B. The leaflets 30a, 30b, 30c are heat set at the same or similar time and temperature conditions as described above.

The leaflets 30a, 30b, 30c may also be heat set in the closed position, and then the leaflets 30a, 30b, 30c may be heat set a second time in the open position, or vice versa. Alternatively, the leaflets 30a, 30b, 30c may be heat set simultaneously to bias a portion of each leaflet to the closed condition and another portion of each leaflet to the open condition. That is, it is contemplated that the leaflets 30a, 30b, 30c may be heat set both to fully coapt and eliminate any gap 23 in the closed condition, and also to open to the maximum opening position in which the free edges 32a, 32b, 32c do not extend into the valve opening area 33. As noted, this may be done in separate steps using separate forming devices as described below, or in a single step in which the forming device is able to contour both portions of the leaflet simultaneously.

Heat setting the leaflets can be done at different stages in the prosthetic valve manufacturing process. As described above, the heat setting process may be performed after the valve is manufactured. Performing the heat setting process after the valve is manufactured may be advantageous because the standard manufacturing procedures of fabricating a prosthetic heart valve can be followed. However, if heat setting of the synthetic leaflet(s) is performed after the valve is manufactured, each valve component, in addition to the synthetic leaflets, may need to be tolerant of heat. Heat setting after the valve is manufactured is further illustrated in FIGS. 4A1-4A3, 4B1-4B3, and 4C1-4C2.

FIGS. 4A1-4A3 illustrate a prosthetic heart valve 100 that has been manufactured to include three prosthetic leaflets 40a, 40b, 40c that are formed of a synthetic material, such as UHMWPE. FIGS. 4A1 and 4A3 illustrate top views of the valve 100 when the leaflets are in the open and closed positions, respectively, similar to FIGS. 2A and 3A. FIG. 4A2 illustrates a perspective view of the prosthetic heart valve 100 with the leaflets in the closed position. As illustrated in FIGS. 4A1-4A3, the leaflets 40a, 40b, 40c are attached to a leaflet support (such as a stent) along the sewing region 42 of the leaflets by methods known in the art. For example, the leaflet support may be a plastic stent with three commissure tips and three scalloped portions connecting the commissure tips. One or more cuffs may also be provided on one or both surfaces of the stent, and the cuff may be formed of any suitable material including tissue or synthetic materials, including synthetic materials similar to those described above for fabricating the prosthetic leaflets. The prosthetic heart valve 100 illustrated in FIGS. 4A1-4A3 is a surgical heart valve, and thus includes a sewing cuff 41 positioned around an outer periphery of the stent, the sewing cuff 41 intended to be sutured to the native valve annulus to fix the prosthetic heart valve 100 in place. At this stage, the manufacturing process to prepare a prosthetic heart valve has been performed in a conventional manner and heat setting of the leaflets has not yet taken place. Prosthetic heart valves having generally similar structure are described in greater detail in U.S. Pat. No. 6,936,067, the disclosure of which is hereby incorporated by reference herein. Several methods may be used to help ensure that optimal coaptation is achieved after the leaflets are heat set. For example, the leaflets 40a, 40b, 40c may be tacked together using a suture (or other similar mechanical fixation), or the leaflets may be disposed on a mandrel, to provide a desired shape to the leaflets during the heat setting procedure. In FIGS. 4B1-4B3, leaflets 40a, 40b, 40c are reversibly tacked together using a suture 43 such that the free edges 44a, 44b, 44c are in contact with one another with little to no gap in the center of the valve opening area 45. In other words, the free edges 44a, 44b, 44c of leaflets 40a, 40b, 40c are temporarily fixed in a preferred coapted condition (e.g., with the free edges of the leaflets having matching configurations) with suture 43. Suture 43 may include a plurality of whip stiches over the free edges 44a, 44b, 44c. Suture 43 ensures that the opposed free edges 44a, 44b, 44c of leaflets 40a, 40b, 40c match one another. An additional suture 46 may temporarily be fixed to the leaflets 40a, 40b, 40c to provide a force on the leaflets 40a, 40b, 40c that generally simulates the pressure that the leaflets would experience from retrograde blood flow forcing the leaflets into the closed position. This force from the additional suture 46 may confer a curved shape to the leaflets 40a, 40b, 40c and form a coaptation depth in the leaflets 40a, 40b, 40c while the suture 46 is attached to the leaflets 40a, 40b, 40c. The additional suture 46 may also couple the leaflets together such that the additional suture 46 goes through all three leaflets 40a, 40b, 40c. The additional suture 46 may be secured to the leaflets 40a, 40b, 40c at different distances below the free edges 44a, 44b, 44c. For example, the additional suture 46 may be secured about 1 mm below the free edges, about 1.5 mm below the free edges, about 2 mm below the free edges, about 2.5 mm below the free edges, about 3 mm below the free edges, or about 3.5 mm below the free edges. The additional suture 46 may also be included on various profiles to achieve the desired coaptation depth and/or provide a desired contour in the leaflet. For example, in FIGS. 4B1-4B3, the additional suture 46 extends generally linearly below the free edges 44a, 44b, 44c, while in FIG. 5 the additional suture profile 46b may be non-linear to form an alternative contour in the leaflet. Though two sutures (43 and 46) are shown in FIGS. 4B1-3 and FIG. 5, any number of sutures may be used to produce the desired shape of the leaflets. Although sutures are described above as one way of temporarily providing a desired shape to the leaflets prior to heat setting (e.g., by providing matching coaptation edges and/or providing desired contouring and/or coaptation depths), other mechanisms may be used in place of sutures to provide a similar effect. For example, one or more mechanized dies may be movable in a specified motion path to force the leaflets against one another, preparing the leaflets for optimal positioning prior to performing the heat setting process. Other mechanical methods to secure the leaflets in a desired position and/or orientation for heat setting may be similarly applied.

Once the sutures 43 and 46 are secured to the leaflets 40a, 40b, 40c, a heat setting process may be performed. In one embodiment, the heat setting process may be performed for between about 20 seconds and about 30 minutes. In additional embodiments, the heat setting process may be performed for between about 2 minutes and about 20 minutes, or between about 5 minutes and about 10 minutes, but is not limited to these times. In one embodiment, the heat setting process may also be performed at a temperature between about 90° C. and about 170° C. In additional embodiments, the heat setting process may be performed at a temperature between about 110° C. and about 150° C., or between about 120° C. and about 135° C. Once the heat setting process is complete, the valve 100 is allowed to cool. After the valve has cooled, sutures 43 and 46 are removed from the leaflets 40a, 40b and 40c and a contoured leaflet is obtained, as can be seen in FIGS. 4C1-4C2. In FIGS. 4C1-4C2, it can be seen that the free edges 44a, 44b, and 44c more closely coapt with one another after heat setting compared to before heat setting in FIGS. 4A1-4A3.

Although the embodiments above have generally described heat treatment of the synthetic leaflets of a surgical valve, it should be understood that the same concepts may apply to other types of prosthetic heart valves utilizing synthetic leaflets, including those having collapsible and expandable stents. For example, a prosthetic heart valve having a collapsible and expandable stent, one or more cuffs, and a plurality of prosthetic leaflets formed of a synthetic material may be manufactured according to known methods. In the same manner as described above for the surgical heart valve, the synthetic leaflets of the collapsible heart valve may be temporarily tacked together and heat set to provide the same benefits as described above.

In other embodiments, heat setting may alternatively (or additionally) be performed earlier in the valve manufacturing process, including before the leaflets are attached to the support structure. That is, individual synthetic leaflets may be heat set prior to being attached to the support structure. It should be understood that this includes heat setting a plurality of synthetic leaflets that are already attached to one another, but still prior to the leaflets being attached to the support structure. For example, this concept may apply to a situation in which individual leaflets are formed and then attached to one another. This concept may further apply to a situation in which a single strip of synthetic material is formed into a group of interconnected leaflets, prior to the single strip of material being coupled to the support structure. Heat setting individual leaflet components may be advantageous because it may be more efficient when manufacturing the valve. Heat setting individual leaflet components may also allow for more uniform heat setting because each leaflet may be constrained in a separate mold. Further, heat setting individual leaflet components may be advantageous because less overall time may be needed to heat set an entire valve, as compared to heat setting a valve when the leaflets are attached to a support structure, such as a stent. Additionally, by heat setting individual leaflets, greater design flexibility for the valve can be obtained because non-leaflet components would not have to be heat resistant, allowing for a potentially greater choice in materials for use in the prosthetic heart valve.

To obtain the desired coaptation and shape of the individual leaflets from the heat setting procedure, a fixture or mandrel may be used instead of a suture as described above. There may be a benefit in avoiding the use of temporary sutures such as those described above in connection with FIGS. 4B 1-4B3, as the removal of those sutures after heat setting could disrupt the leaflet material, with such disruption potentially causing a loss of the structural integrity of the leaflet or introducing leakage through the holes left by the suture. There may be still other benefits to heat setting the leaflets prior to their attachment to one another and/or prior to their attachment to a support structure, like a stent. For example, it may be easier from an operational standpoint to deal with individual leaflets rather than an entire valve assembly (or even a valve sub-assembly). Further, if any non-conforming parts are identified during the process, those parts may be discarded, which may be easier and less expensive than discarding non-conforming parts after a valve has been partially or fully assembled.

The individual leaflets may be heat set in either the open position, the closed position, or portions of the leaflets may be heat set in the open position and other portions of the leaflets may be heat set in the closed position. It should be understood that, preferably, each leaflet is heat set in the same position (i.e., it is preferable that all of the leaflets are heat set in the open position, or all of the leaflets are heat set in the closed position, or portions of all of the leaflets are heat set in the open position and other portions of all of the leaflets are heat set in the closed position). FIGS. 6A1, 6A2, 6B1, 6B2, 6C1, 6C2, 6D1 and 6D2 illustrate heat setting of the leaflets in the closed position using a mandrel. In the embodiment illustrated in FIGS. 6A1, 6A2, 6B 1, 6B2, 6C1, 6C2, 6D1 and 6D2, the plurality of leaflets are provided as a single circular or tubular continuous strip of synthetic material. However, it should be understood that a similar process could be used if the synthetic leaflets were individually formed and then coupled together, for example via sutures. FIGS. 6A1-6A2 illustrate top and side views, respectively, of three leaflet components 60a, 60b, 60c fabricated from UHMWPE. The mandrel may include any mandrel known in the art to achieve the desired leaflet profile for a prosthetic heart valve. In one embodiment, the mandrel may be cylindrical with contours either cut into the mandrel or embossed out of it. In another embodiment, a single or multiple contoured surface mandrel may be used to achieve the desired leaflet profile. In some embodiments, for example when the leaflets are provided as a sub-assembly prior to attachment to a support structure like a stent, a double-mandrel may be provided, in which the two mandrels cooperate to sandwich the leaflets prior to heat setting. The two mandrels can thus be positioned on the inflow and outflow sides of the leaflets, respectively, and have the desired opposite (or complementary) contours to one another. In other words, one mandrel may include concave contours corresponding to the desired leaflet shape on one side of the leaflet, and the other mandrel may include convex contours corresponding to the desired leaflet shape on the other side of the leaflet. For example, in FIGS. 6B1-6B2 and 6C1-6C2, the mandrel 61 may be a 29 mm fixation mandrel (e.g., a mandrel having an outer diameter of about 29 mm, although other sized mandrels may be suitable).

The mandrel 61 may be formed of any suitable rigid material, preferably one that is heat tolerant and able to transfer heat efficiently. In one embodiment, the outer surface of the mandrel 61 may have a shape that corresponds to the shape which the leaflets 60a, 60b, 60c preferably have when the leaflets are under the pressure of retrograde blood flow in the closed condition. For example, the mandrel 61 may include a portion having a three-pointed star or three-bladed shape. For example, three blades may join together at a longitudinal center of the mandrel 61, with each blade extending radially outward from the longitudinal center and narrowing toward a tip of each blade. Each blade may be positioned at substantially equal circumferential intervals around the mandrel 61, including, for example, at intervals of about 120 degrees. However, it should be understood that other shaped mandrels may be suitable, for example a two-bladed mandrel for a prosthetic valve with two leaflets.

In FIGS. 6B 1-6B2, the leaflets 60a, 60b, 60c are secured to the mandrel 61 using clips 62a, 62b, 62c. In particular, the transition between adjacent leaflets is aligned with one of the blades, and a clip is placed over the transition point near the free edges of the adjacent leaflets, extending toward the longitudinal center of the mandrel 61. With this configuration, each leaflet 60a, 60b, 60c is contacted by two clips—in other words, one clip is used per commissure. Once the clips 62a, 62b, 62c are attached to the mandrel, a heat setting process may be performed. In one embodiment, the heat setting process may be performed for between about 20 seconds and about 30 minutes. In additional embodiments, the heat setting process may be performed for between about 2 minutes and about 20 minutes, or between about 5 minutes and about 10 minutes, but is not limited to these times. In one embodiment, the heat setting process may also be performed at a temperature between about 90° C. and about 170° C. In additional embodiments, the heat setting process may be performed at a temperature between about 110° C. and about 150° C., or between about 120° C. and about 135° C. FIGS. 6C1-6C2 illustrate the heat set leaflets once the clips 62a, 62b, 62c have been removed from the leaflets 60a, 60b, 60c, but while the leaflets are still on the mandrel 61. FIGS. 6D1-6D2 illustrate the heat set leaflets 60a, 60b, 60c after having been removed from the mandrel 61. It can be seen that the leaflets have a shape set to the desired closed configuration, with the leaflets being substantially uniform along the free edges 63a, 63b, 63c.

Figure 7A:
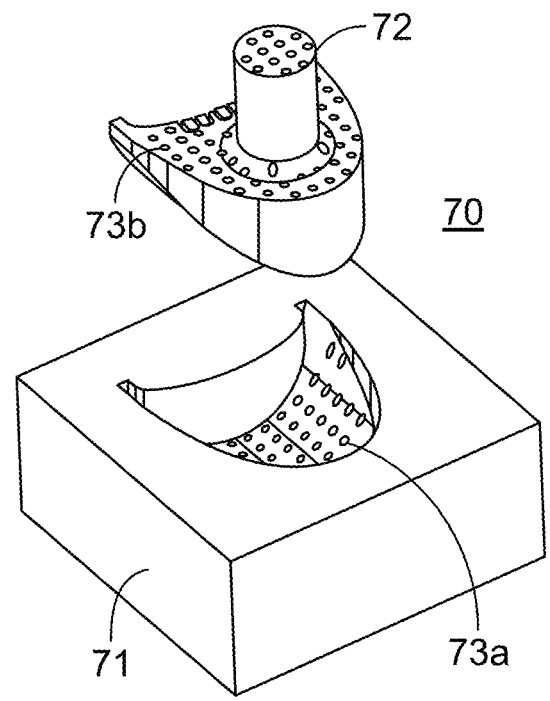
FIG. 7A is a perspective view of a mold for heat setting a leaflet according to another embodiment of the present disclosure, the mold having a base and insert shown spaced apart from each other.
Figure 7B:
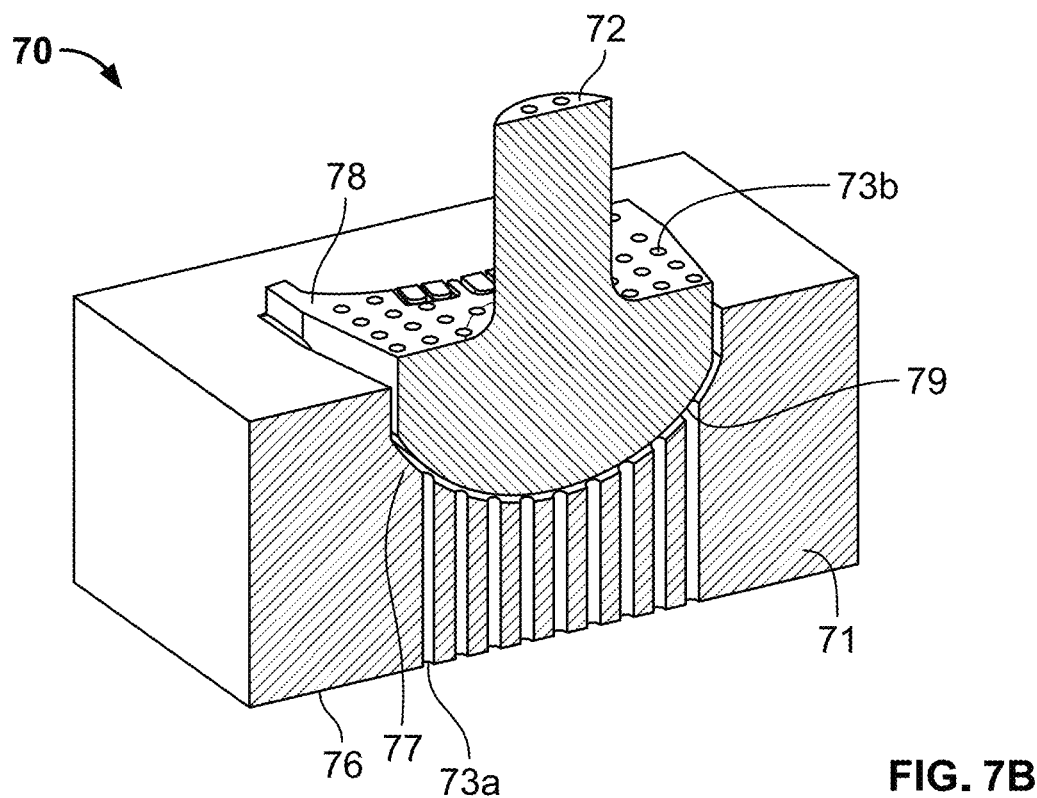
FIG. 7B is a cross-section of the mold of FIG. 7A in the operational position in which the insert is received within the base.

In another embodiment, prior to valve assembly, individual leaflets of the present disclosure may be heat set in the closed position using a mold as illustrated in FIGS. 7A and 7B. It should be understood that, while the embodiment described in connection with FIGS. 6A-D pertains to heat setting a pre-formed leaflet strip that includes all of the leaflets in one piece of material, the embodiment described below in connection with FIGS. 7A-B pertains to heat setting one or more individual leaflets that will later be coupled together to form a valve assembly. However, in other embodiments, the mandrel concept described above in connection with FIGS. 6A-D may be utilized with individual leaflets that will later be coupled together to form a valve assembly, while the mold concept described below in connection with FIGS. 7A-B could be used with a leaflet strip similar to that described in connection with FIGS. 6A-D.

In FIG. 7A, a mold 70 includes a base 71 and an insert 72. The base 71 may include a recess shaped to the desired dimensions of the leaflet for use in a prosthetic heart valve. For example, the recess in the base 71 may be shaped to correspond to a desired shape of the leaflet while the leaflet is under pressure from retrograde blood flow in the closed condition. The insert 72 may include a leading bottom surface that has a corresponding or complementary shape to the recess in the base 71, so that the leading bottom surface of the insert 72 closely and uniformly contacts the recessed surface in the base 71 as the insert 72 is pressed into the base 71. Vent holes 73a, 73b may also be included in the base 71 and insert 72, respectively. The vent holes 73a in the base 71 may be substantially aligned with the vent holes 73b in the insert 72 when the insert is inserted into the base. Alternatively, the vent holes 73a in the base 71 may be offset from the vent holes 73b in the insert 72. Any number of vent holes 73a, 73b may be included in the base 71 and insert 72. In use, the vent holes 73a, 73b may help heat to be uniformly applied to the leaflet (not shown) when the heat setting process is performed.

To perform the heat setting process, various heating mechanisms may be used. In one embodiment, a leaflet (not pictured) is placed in the base 71 of the mold 70. The insert 72 is then placed on top of the leaflet in the mold 70. After the leaflet is placed in the mold 70, the mold 70 may be placed in a chamber in which the air within the chamber is heated. Thus, the leaflet inside of the mold 70 may be heated by ambient heat. In another embodiment, after the leaflet is placed in the mold 70, the insert 72 and base 71 may be directly heated, which allows the leaflet to be heat set. In a further embodiment, hot air may be blown through vent holes 73a, 73b which may heat the leaflet in the mold 70. To speed up the heat setting process, the insert 72 and base 71 of the mold 70 may be heat conductive.

FIG. 7B is a cross-section of the mold in FIG. 7A illustrating the insert 72 received within the recess of the base 71. As can be seen in FIG. 7B, the vent holes 73*a* extend from the bottom surface 76 of the base 71 to the top surface 77 of the base, where the top surface 77 of the recessed area of the base 71 contacts the leaflet. The vent holes 73*a* are positioned in the base 71 to be in contact with the leaflet when the leaflet is pressed between the base 71 and the insert 72, which allows heat to uniformly be applied to the pressed leaflet. Vent holes 73*b* are also included in the insert 72. Vent holes 73*b* extend from the trailing top surface 78 of the insert 72 to the leading bottom surface 79 of the insert 72, where the bottom surface 79 contacts the leaflet. The vent holes 73*b* in the insert also allow for uniform heat application to the leaflet when the leaflet is pressed between the base 71 and the insert 72. In addition to directing heated air to the surfaces of the leaflet, vent holes 73*a*, 73*b* may supply cooled air to the leaflet surfaces, such as to cool the leaflet within the mold 70 after the heat setting process. As should be understood from the above, in FIGS. 6A-6D and 7A-7B, the mandrel shape or mold shape may be designed to vary the contour of the leaflet to match a desired shape of the leaflet when the leaflet is in the closed position. By being able to control and vary the contour of the leaflet, leaflet motion and coaptation may be optimized.

In one embodiment, the heat setting process using the mold 70 may be performed for between about 20 seconds and about 30 minutes. In additional embodiments, the heat setting process may be performed for between about 2 minutes and about 20 minutes, or between about 5 minutes and about 10 minutes, but is not limited to these times. In one embodiment, the heat setting process may also be performed at a temperature between about 90° C. and about 170° C. In additional embodiments, the heat setting process may be performed at a temperature between about 110° C. and about 150° C., or between about 120° C. and about 135° C.

In an additional embodiment, the individual leaflets may be heat set in an open position as illustrated in FIGS. 8A, 8B1 and 8B2. When the individual leaflets are heat set in the open configuration, the leaflets may open more completely, resulting in a larger effective orifice area of the valve assembly. Another benefit may be that the valve gradient, or the pressure differential needed to open the valve, may be improved as blood flows. In FIG. 8A, the leaflets 80*a*, 80*b* and another leaflet 80*c* (not shown in FIG. 8A) may be attached to a mandrel 81. The mandrel 81 may have a main portion that is substantially cylindrical, and that cylindrical portion may have a diameter that is about equal to the diameter of the stent to be used in the prosthetic heart valve and/or to the desired diameter of the prosthetic heart valve once fully assembled. The leaflets 80*a*, 80*b*, 80*c* may be attached to the mandrel using a clip or rubber band 82 or any other suitable reversible coupling mechanism, preferably one in which the leaflet is forced to be in close contact with the mandrel. For example, it may be preferable to have a clamshell-type outer housing that clamps over the mandrel to ensure that the leaflets are forced to match the curvature of the mandrel 81. The leaflets 80*a*, 80*b*, 80*c* may also be attached to the mandrel by any other suitable methods, including using adhesives, sutures, electrostatic methods or melting methods. Further, it should be understood that the leaflets 80*a*, 80*b*, 80*c* are preferably aligned relative to the mandrel 81 so that an axis extending from the apex of the attachment edge of the leaflet to the trough of the free edge of the leaflet is substantially parallel to a central longitudinal axis of the mandrel 81.

Heat setting is performed while the leaflets 80*a*, 80*b*, 80*c* are attached to the mandrel 81, with the heat setting performed according to the following conditions. In one embodiment, the heat setting process may be performed for between about 20 seconds and about 30 minutes. In additional embodiments, the heat setting process may be performed for between about 2 minutes and about 20 minutes, or between about 5 minutes and about 10 minutes, but is not limited to these times. In one embodiment, the heat setting process may also be performed at a temperature between about 90° C. and about 170° C. In additional embodiments, the heat setting process may be performed at a temperature between about 110° C. and about 150° C., or between about 120° C. and about 135° C. After heat setting, leaflets 80*a*, 80*b*, 80*c* may be removed from the mandrel 81 and attached to the stent to form the prosthetic heart valve. The heat set leaflets 80*a*, 80*b*, 80*c* are shown in FIGS. 8B1-8B2 from top and side views, respectively, in the heat-set open position with uniform free edges 83*a*, 83*b*, 83*c*. Although the heat setting in connection with FIGS. 8A, 8B1 and 8B2 is described for use with pre-cut, individual leaflets, it should be understood that, in some embodiments, a mandrel similar to mandrel 81 may be used to heat set a leaflet strip in the open position, for example a leaflet strip similar to that shown and described in connection with FIGS. 6A1-6A2.

Figure 9A:
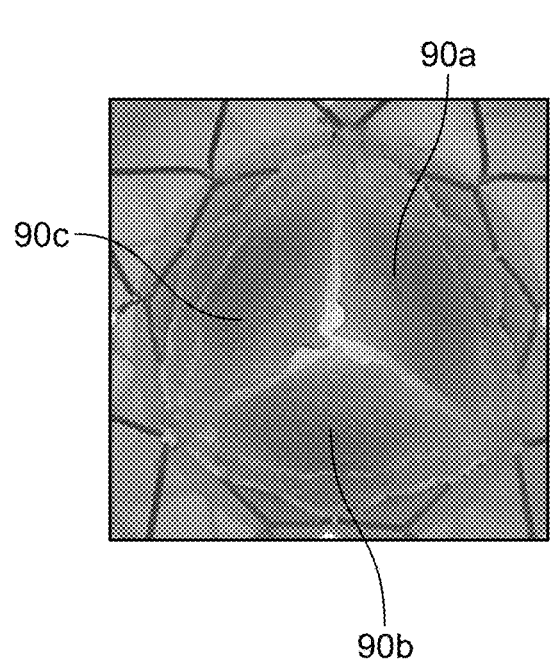
FIG. 9A is a top view of a collapsible prosthetic heart valve illustrating the leaflets in the closed position without having been heat set.
Figure 9B:
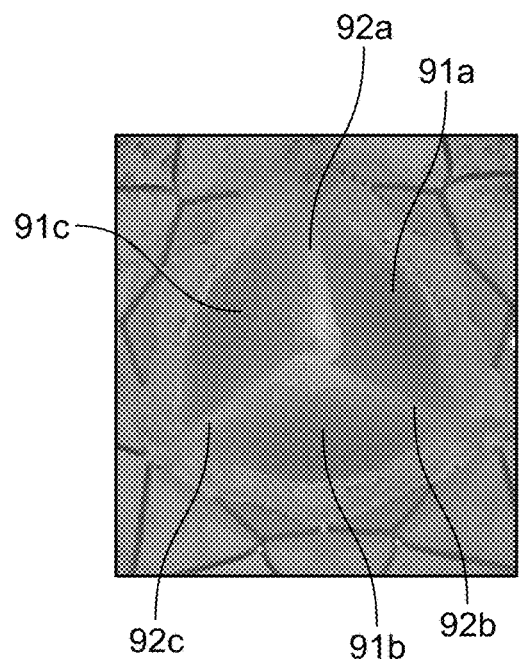
FIG. 9B is a top view of the collapsible prosthetic heart valve of FIG. 9A illustrating the leaflets in the closed position after the leaflets have been heat set.
Figure 10A:
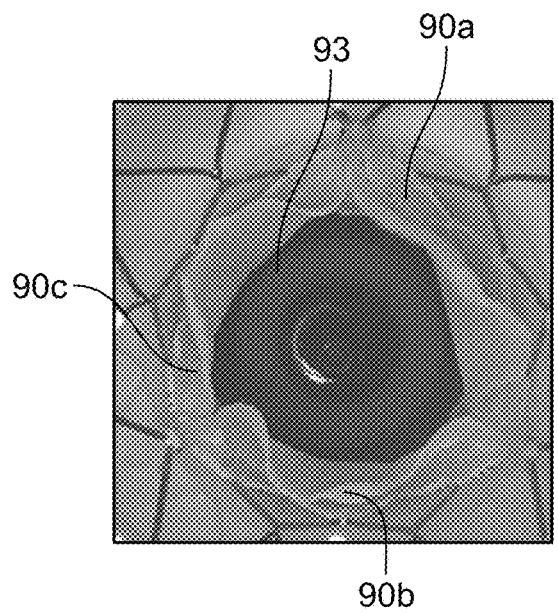
FIG. 10A is a top view of the collapsible prosthetic heart valve of FIG. 9A illustrating the leaflets in the open position without having been heat set.
Figure 10B:
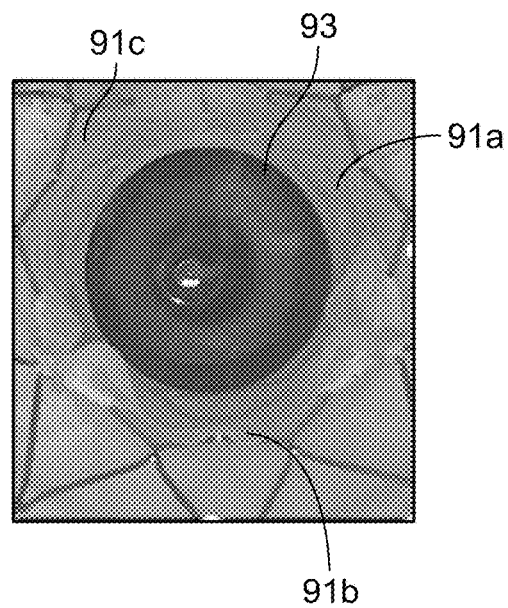
FIG. 10B is a top view of the collapsible prosthetic heart valve of FIG. 9B illustrating the leaflets in the open position after the leaflets have been heat set.

FIGS. 9A and 10A illustrate top views of a collapsible and expandable prosthetic heart valve that has been assembled with synthetic leaflets 90*a*, 90*b*, 90*c*, without any heat setting, whereas FIGS. 9B and 10B illustrate an identical prosthetic heart valve in which the leaflets 91*a*, 91*b*, 91*c* have been heat set into the open condition, for example using the process described above in connection with FIGS. 8A-B. When the leaflets 90*a*, 90*b*, 90*c* of the untreated prosthetic heart valve are in the open condition, shown in FIG. 10A, the leaflets do not open fully over the valve opening area 93. However, as can be seen in FIG. 10B, the heat-treated, heat-set leaflets 91*a*, 91*b*, 91*c* more completely open over the valve opening area 93, which provides better blood flow through the prosthetic heart valve. It should be understood that heat-setting the leaflets into the open condition may not result in worse coaptation when the leaflets are in the closed condition. As can be seen by comparing the free edges of the untreated leaflets 90*a*, 90*b*, 90*c* in the closed condition shown in FIG. 9A to the free edges 92*a*, 92*b*, 92*c* of the heat-set leaflets 91*a*, 91*b*, 91*c* in the closed condition shown in FIG. 9B, both sets of leaflets achieve good coaptation.

In another embodiment, the leaflets may be heat set in a partial assembly. For example, the leaflets may be temporarily pre-attached to the support structure and heat set. After heat setting, the leaflets may be permanently assembled to the support structure.

In another embodiment of the present disclosure, other features may be alternatively or additionally be incorporated into the leaflet by heat setting. For example, one or more pleats, one or more creases and/or one or more folds may be incorporated into one or more of the leaflets at one or more specific locations via heat setting. It should be understood that these features may be created in addition to, or instead of, heat setting the leaflets into the opened and/or closed positions. The pleats, creases or folds may be created across the full length of the leaflet from the attachment edge to the free edge, or across any portion thereof. The properties of the leaflet can be altered based on the number, position, and configuration of the pleats, creases or folds formed in the leaflet. For example, by using pleats, creases or folds, alternating stiffened and more flexible zones or "hinges" may be created. By including alternating stiffened and more flexible zones, a bias may be provided to better control the opening and closing of the leaflet. In other words, the leaflet may be altered so that, based on the positions and number of folds, pleats, or creases, the leaflet will tend to "want" to open or close in a particular and repeatable fashion, including because the folds, pleats, or creases may act as hinges to guide the opening and closing of the leaflet.

In FIGS. 11A-11E dotted lines 1101 represent the locations of the pleats, creases or folds in the leaflet 1100. In the below description of FIGS. 11A-E, the term pleats is used for brevity, but it should be understood that wherever pleats are referred to, creases or folds may instead take the place of the pleats.

In FIG. 11A, three pleats are illustrated in the leaflet. The three illustrated pleats include a first pleat extending substantially parallel to the inflow-to-outflow direction and extending substantially the entire length from the attachment or sewing edge of the leaflet (at the bottom of the leaflet as shown in FIG. 11A) to the free edge of the leaflet (at the top of the leaflet as shown in FIG. 11A). This first pleat is shown positioned at a center of the leaflet (e.g., from the trough of the free edge toward the apex of the attachment edge). Two additional pleats are illustrated in FIG. 11A, with each of the two additional pleats having a first end positioned at about the same location near the attachment edge of the leaflet as the center pleat. The two additional pleats extend substantially diagonally in opposition directions from one another toward respective leaflet tabs positioned at the transition of the leaflet attachment edge to the leaflet free edge.

FIG. 11B illustrates a pleat configuration that is generally similar to that of FIG. 11A, including a center pleat extending substantially parallel to the inflow-to-outflow direction and substantially the entire length of the leaflet from the attachment edge to the free edge. However, instead of two additional diagonal pleats, the embodiment of FIG. 11B includes two additional pleats extending substantially parallel to the center pleat and also from the attachment edge to the free edge, but at spaced distances from the center pleat. As illustrated, the two additional pleats are positioned at about the same lateral distance from the central pleat, but in opposite directions, and meet the free edge of the leaflet near where the free edge transitions into the leaflet tabs.

The embodiment of FIG. 11C is illustrated with only a single pleat. The single pleat of FIG. 11C has a curved contour that substantially follows the curved contour of the attachment edge of the leaflet, but is spaced a short distance therefrom. In other words, the single pleat of FIG. 11C has its ends positioned at or near the opposing tabs of the leaflet, and extends from each end toward a location spaced from the apex of the attachment edge, with the pleat being positioned adjacent the entire length of the attachment edge.

The pleat configurations described above are merely exemplary, and any configuration or combination of pleats is contemplated. For example, FIG. 11D illustrates a leaflet having a combination of the pleat of FIG. 11C and the pleats of FIG. 11A, while FIG. 11E illustrates a leaflet that combines the pleat of FIG. 11C with the pleats of FIG. 11B.

Each of the pleat configurations of FIGS. 11A-E has a generally similar goal of assisting the belly of the leaflet open in a predetermined and repeatable configuration when under pressure from retrograde blood flow to maximize coaptation with the other leaflets and reduce or eliminate any gaps between the leaflets when they coapt. The pleats may also assist the leaflets to fully open during antegrade blood flow to maximize the effective orifice area of the valve assembly when the leaflets are in the opened condition. Although five specific examples of pleat configurations are shown, any and all configurations of pleats (and creases and folds) are contemplated herein, including combinations of the pleat configurations described above. Thus, it should be understood that modifications may be made to the pleat configurations while remaining within the scope of the disclosure. For example, a single center pleat may be provided as shown in FIGS. 11A-B instead of three pleats, curved pleats like the one shown in FIG. 11C may be combined with the center pleat shown in FIGS. 11A-B, and still other configurations may be suitable to create the preferential opening (and/or closing) motion of the leaflets.

Figure 12C:
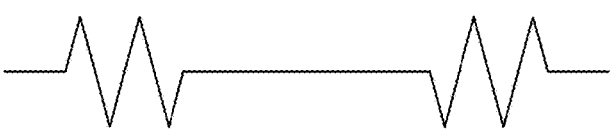
FIG. 12C is a cross-section of the leaflet taken along line A-A of FIG. 11C.

To better illustrate the pleats, creases and folds, FIGS. 12A-12C are cross-sections of the leaflets shown in FIGS. 11A-11C, respectively, taken along line A-A. Therefore, FIGS. 12A-12C show the cross-section of the pleats in the leaflets. It should be understood that, unless indicated otherwise below, the terms pleat, fold and crease are being used interchangeably with one another. And it should be understood that any of the pleats illustrated in FIGS. 11A-E could be formed with any of the pleat cross-sections illustrated in FIGS. 12A-C. FIG. 12A actually illustrate two separate options for a pleat. FIG. 12A1 corresponds to three simple creases made in the otherwise flat material (i.e., the three creases or pleats of FIG. 11A), with the peak of each crease pointing away from the exterior side of the leaflet (i.e., the peaks of the creases will face the stent, or away from the longitudinal center of the prosthetic heart valve, when the leaflets are assembled to the stent). FIG. 12A2, on the other hand, corresponds to three simple creases made in the otherwise flat material (i.e., the three creases or pleats of FIG. 11A), with the peaks of the creases pointing away from the interior surface of the leaflet (i.e., the peaks of the creases will face the longitudinal center of the prosthetic heart valve when the leaflets are assembled the stent). FIG. 12B similarly illustrate two separate options for a pleat. FIG. 12B correspond to the center pleat in FIG. 11B, wherein the pleat includes two creases made in series. The configuration of the pleat of FIG. 12B 1 is similar to creating two of the creases of FIG. 12A1 in series with each other. Thus, the peaks of each crease point away from the exterior side of the leaflet (i.e., the peaks of the creases will face the stent, or away from the longitudinal center of the prosthetic heart valve, when the leaflets are assembled to the stent). However, the peaks of the pleat or double crease could also be formed to face the longitudinal center of the prosthetic heart valve once the leaflets are assembled to the stent, as shown in FIG. 12B2. Finally, the pleat of FIG. 12C (i.e., the single pleat of FIG. 11C that is crossed twice by section line A-A) illustrates creases that extend on both sides of the otherwise flat material of the leaflet. Thus, when the leaflets having the pleat configuration of FIG. 12C are assembled to the stent to form the prosthetic heart valve, the peaks of the creases may point toward the longitudinal center of the prosthetic heart valve and also toward the stent. It should be understood that the pleat configurations of FIGS. 12A-C are illustrative of particular examples of how to shape a pleat, but these particular examples should not be thought of as limiting.

As noted above, the pleats, creases of folds may be incorporated into a leaflet that is heat set when the leaflet is attached to the valve or as an individual leaflet, and the pleats, creases or folds may be provided in addition to, or as an alternative to, the general heat setting described above. Any suitable mechanism may be used to apply the pleats, creases or folds. For example, the leaflets may be heat set to form the creases entirely separately from any of the forming devices above (e.g., without using any of the various molds or mandrels described above). In some examples, a leaflet or leaflets may be folded to temporarily form the pleat, and the leaflet(s) may be heated while temporarily folded to heat set the fold into the leaflet(s). In other embodiments, the molds or mandrels described above may include features to temporarily create pleats in the leaflets, with the heat setting process making the pleats permanent. For example, referring to the mold 70 of FIGS. 7A-B, the leading surface of the insert 72 and/or the recessed surface of the base 71 may have their surfaces modified in order to press the creases into the leaflets when the insert 72 is received in the base 71. For example, the insert 72 may include peaks that are received in troughs of the recessed surface of the base 71 in order to form the creases in the leaflet during heat setting. Other molds or mandrels described herein may be similarly modified in order to be able to heat set the leaflet into the opened or closed position while simultaneously heat setting the creases, folds, or pleats in the desired configuration.

According to one embodiment of the disclosure, a prosthetic heart valve includes a stent; and a valve assembly attached to a stent, the valve assembly including a cuff and a plurality of prosthetic leaflets, each of the prosthetic leaflets being composed of a synthetic material, the prosthetic leaflets having a closed condition in which the prosthetic leaflets coapt to restrict blood from flowing in a retrograde direction through the stent, and an open condition in which the prosthetic leaflets allow blood to flow in an antegrade direction through the stent, wherein the synthetic material of at least one of the prosthetic leaflets may bias the prosthetic leaflet toward either the closed condition or the open condition; and/or
  the synthetic material of the at least one prosthetic leaflet may bias the prosthetic leaflet toward the closed condition; and/or
  the synthetic material of the at least one prosthetic leaflet may bias the prosthetic leaflet toward the open condition; and/or
  the synthetic material of the at least one prosthetic leaflet may bias a portion of the prosthetic leaflet toward the closed condition and another portion of the prosthetic leaflet toward the open condition; and/or
  the synthetic material may be ultra-high molecular weight polyethylene.

According to another embodiment of the disclosure, a prosthetic heart valve includes a stent; and a valve assembly attached to the stent, the valve assembly including a cuff and a plurality of prosthetic leaflets, each of the prosthetic leaflets being composed of a synthetic material and having an attachment edge attached to the stent and a free edge, the prosthetic leaflets having a closed condition in which the prosthetic leaflets coapt to restrict blood from flowing in a retrograde direction through the stent, and an open condition in which the prosthetic leaflets allow blood to flow in an antegrade direction through the stent, wherein the synthetic material of one of the leaflets may include a fold or crease formed between the attachment edge and the free edge to assist the prosthetic leaflet in transitioning between the closed condition and the open condition in a particular and repeatable desired movement; and/or
  the synthetic material of the one prosthetic leaflet may include a first fold or crease extending from an apex of the attachment edge of the leaflet to a trough of the free edge of the leaflet in a direction substantially parallel the antegrade direction of blood flow through the stent; and/or
  the synthetic material of the one prosthetic leaflet may include a second fold or crease and a third fold or crease each extending from the attachment edge of the leaflet to the free edge of the leaflet; and/or
  the second fold or crease and the third fold or crease may each be substantially parallel to the first fold or crease, the first fold or crease being positioned between the second fold or crease and the third fold or crease; and/or
  the second fold or crease and the third fold or crease may each extend in substantially opposite diagonal directions from the attachment edge of the leaflet to the free edge of the leaflet, the first fold or crease being positioned between the second fold or crease and the third fold or crease; and/or
  the synthetic material of the one prosthetic leaflet may include a first fold or crease extending in an arcuate direction substantially matching a curvature of the attachment edge of the leaflet.

According to another embodiment of the present disclosure, a method of manufacturing a prosthetic heart valve includes preparing a synthetic material; forming a bias in the synthetic material by heat setting the synthetic material at a temperature of between about 90° C. and about 170° C. for between about 20 seconds and about 30 minutes; and coupling the synthetic material to a support structure to form one or more leaflets so that the leaflets are (i) biased toward a closed condition in which the leaflets coapt to restrict blood from flowing in a retrograde direction through the support structure, or (ii) biased toward an open condition in which the leaflets allow blood to flow in an antegrade direction through the support structure; and/or
  a portion of at least one leaflet may be biased to the closed condition and another portion of the at least one leaflet may be biased to the open condition; and/or
  the method may further include disposing the synthetic material on a mandrel before heat setting the synthetic material; and/or
  disposing the synthetic material on the mandrel may include shaping the synthetic material into a shape that corresponds to the closed condition; and/or
  disposing the synthetic material on the mandrel may include shaping the synthetic material into a shape that corresponds to the open condition; and/or
  the synthetic material may be a single strip of synthetic material during the heat setting of the synthetic material, the single strip of synthetic material forming a plurality of the leaflets after being coupled to the support structure; and/or
  the method may further include securing the synthetic material to a mandrel at a number of locations spaced equidistantly around a circumference of the mandrel prior to heat setting the synthetic material, the number of locations corresponding to a number of leaflets formed by the single strip of synthetic material; and/or
  the synthetic material may be coupled to the support structure prior to heat setting the synthetic material; and/or
  heat setting the synthetic material may include pressing the synthetic material into a base of a mold using an insert and applying heat while the insert presses the synthetic material into the base of the mold; and/or
  the method may include disposing the synthetic on a mandrel prior to heat setting the synthetic material, wherein the mandrel has a cylindrical shape having a diameter that is substantially equal to a diameter of the support structure when the support structure is in an operative condition; and/or the synthetic material may be formed as a single leaflet during the heat setting of the synthetic material, and, after coupling the synthetic material to the support structure, the single leaflet is one leaflet of a plurality of leaflets coupled to the support structure.

Although the present disclosure has been made with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims. For example, features of one embodiment described above may be combined with features of other embodiments described above.

The invention claimed is:

1. A prosthetic heart valve, comprising:
a support structure; and
a valve assembly attached to the support structure, the valve assembly including a cuff and a plurality of prosthetic leaflets, each leaflet in the plurality of prosthetic leaflets being composed of a synthetic material, the plurality of prosthetic leaflets having a closed condition in which the plurality of prosthetic leaflets coapt to restrict blood from flowing in a retrograde direction through the support structure, and an open condition in which the plurality of prosthetic leaflets allow blood to flow in an antegrade direction through the support structure, the plurality of prosthetic leaflets not having a condition which purposefully enables blood to flow in the retrograde direction through the support structure,
wherein the synthetic material of at least one of the prosthetic leaflets in the plurality of prosthetic leaflets is heat set in both the closed condition and the open condition.

2. The prosthetic heart valve of claim 1, wherein the synthetic material is ultra-high molecular weight polyethylene.

3. The prosthetic heart valve of claim 1, wherein the synthetic polymeric material has a thickness of 250 µm or less.

4. The prosthetic heart valve of claim 1, wherein the synthetic polymeric material has a tensile strength of at least 75 N.

5. The prosthetic heart valve of claim 1, wherein the synthetic polymeric material has a stiffness/flexural rigidity of 3.0+/−1.75 cm.

6. The prosthetic heart valve of claim 1, wherein the synthetic polymeric material has a permeability of 850-950 mL/cm2/min.

7. The prosthetic heart valve of claim 1, wherein the synthetic polymeric material has a suture retention meeting ISO7198.

8. The prosthetic heart valve of claim 1, wherein the synthetic polymeric material has a stretch/strain of 20-25%.

9. The prosthetic heart valve of claim 1, wherein the synthetic polymeric material has a tear strength meeting or exceeding ASTM D2261-13.

10. The prosthetic heart valve as claimed in claim 1, wherein a first portion of the at least one prosthetic leaflet is heat set in the closed condition and a second portion of the at least one prosthetic leaflet is heat set in the open condition.

11. The prosthetic heart valve as claimed in claim 10, wherein the first portion of the at least one prosthetic leaflet is heat set in the closed configuration and the second portion of the at least one prosthetic leaflet is heat set in the open configuration simultaneously.

12. The prosthetic heart valve as claimed in claim 1, wherein the at least one prosthetic leaflet is heat set in the closed condition and in the open condition sequentially.

13. The prosthetic heart valve as claimed in claim 1, wherein a commissure region of the at least one prosthetic leaflet is heat set in a closed configuration and a middle of the at least one prosthetic leaflet is heat set in an open configuration.

14. The prosthetic heart valve as claimed in claim 1, wherein a free edge of the at least one prosthetic leaflet is heat set in a closed configuration and a belly of the at least one prosthetic leaflet is heat set in an open configuration.

15. A prosthetic heart valve, comprising:
a support structure; and
a valve assembly attached to the support structure, the valve assembly including a cuff and a plurality of prosthetic leaflets, each leaflet in the plurality of prosthetic leaflets being composed of a synthetic polymeric material and having an attachment edge attached to the support structure and a free edge, the plurality of prosthetic leaflets having a closed condition in which the plurality of prosthetic leaflets coapt to restrict blood from flowing in a retrograde direction through the support structure, and an open condition in which the plurality of prosthetic leaflets allow blood to flow in an antegrade direction through the support structure, the plurality of prosthetic leaflets not having a condition which purposefully enables blood to flow in the retrograde direction through the support structure,
wherein the synthetic material of one of the prosthetic leaflets in the plurality of prosthetic leaflets includes a first heat set fold or crease extending in an arcuate direction substantially matching a curvature of the attachment edge of the one prosthetic leaflet and a second heat set fold or crease extending only from the first fold or crease toward the free edge to assist the one prosthetic leaflet in transitioning between the closed condition and the open condition in a particular and repeatable desired movement.

16. The prosthetic heart valve of claim 15, wherein the second fold or crease extends from an apex of the first heat set fold or crease to a trough of the free edge of the one prosthetic leaflet in a direction substantially parallel to the antegrade direction of blood flow through the support structure.

17. The prosthetic heart valve of claim 16, wherein the synthetic material of the one prosthetic leaflet includes a third heat set fold or crease and a fourth heat set fold or crease each extending only from the first fold or crease of the one prosthetic leaflet to the free edge of the one prosthetic leaflet.

18. The prosthetic heart valve of claim 17, wherein the third fold or crease and the fourth fold or crease are each substantially parallel to the second fold or crease, the second fold or crease being positioned between the third fold or crease and the fourth fold or crease.

19. The prosthetic heart valve of claim 17, wherein the third fold or crease and the fourth fold or crease each extend in substantially opposite diagonal directions from the first fold or crease of the one prosthetic leaflet to the free edge of the one prosthetic leaflet, the second fold or crease being positioned between the third fold or crease and the fourth fold or crease.

\* \* \* \* \*